United States Patent [19]

Day et al.

[11] 4,255,334
[45] Mar. 10, 1981

[54] PROCESS FOR PREPARING 3-AZABICYCLO(3.1.0)HEXANE-2-CARBOXYLIC ACID

[75] Inventors: Janet A. Day, Gillingham; Barry R. J. Devlin, Sittingbourne; Robert J. G. Searle, Rodmersham Green, all of England

[73] Assignee: Shell Oil Company, Houston, Tex.

[21] Appl. No.: 49,374

[22] Filed: Jun. 18, 1979

[30] Foreign Application Priority Data

Jun. 27, 1978 [GB] United Kingdom ............... 27978/78

[51] Int. Cl.$^3$ .................. C07D 207/20; C07D 207/22
[52] U.S. Cl. ............................................. 260/326.5 B
[58] Field of Search .................................. 260/326.5 B

[56] References Cited

U.S. PATENT DOCUMENTS 4,047,930  9/1977  Kerr ......................................... 71/95

Primary Examiner—Jose Tovar

[57] ABSTRACT

3-Azabicyclo(3.1.0)hexane-2-carboxylic acid, a plant gametocide, is prepared by effecting reaction between cis 2-aminomethylcyclopropyl-1,1-dimethyl acetal and a cyanide in the presence of a liquid lower-alkanecarboxylic acid; treating the resulting N-alkanoyl-3-azabicyclo(2.1.0)hexane-2-carbonitrile with a strong acid; treating the resulting 3-alkanoyl-3-azabicyclo(3.1.0)hexane-2-carboxylic acid with strong acid to form the desired 3-azabicyclo(3.1.0)hexane-2-carboxylic acid.

4 Claims, No Drawings

PROCESS FOR PREPARING 3-AZABICYCLO(3.1.0)HEXANE-2-CARBOXYLIC ACID

BACKGROUND TO THE INVENTION 3-azabicyclo(3.1.0)hexane-2-carboxylic acid has been found to be an effective plant male gametocide: U.S. Pat. No. 4,047,930 (the compound is designated therein as 2-carboxy-3,4-methanopyrrolidine). The compound exists in the forms of two geometric (i.e., cis, trans) isomers. Each of these isomeric forms exists in the forms of optical isomers. The racemic mixtures of both of the geometric isomer forms are active as plant male gametocides. The naturally occurring L,cis isomer is active as a plant male gametocide; the relative activities of each of the other optical isomer forms have not been determined. The L,cis isomer occurs naturally in the seeds of the American horse chestnut.

*Aesculus parviflora.*

3-azabicyclo(3.1.0)hexane-2-carboxylic acid now can be prepared synthetically by the following route:

(1) cis-ethyl 2-cyanocyclopropylcarboxylate (Zhur. Org. Khim., 7, 2108 et seq. (1971)) is treated with sodium hydroxide and the product is acidified to spring the acid.

(2) The acid is treated with oxalyl chloride in benzene to form the crude 2-cyanocyclopropyl acid chloride.

(3) The crude acid chloride is treated with a reducing agent, such as tri-(tertiary-butoxy) lithium aluminum hydride, in tetrahydrofuran, at a low temperature (e.g., −60° C.) to form crude 2-cyanocyclopropyl aldehyde.

(4) The crude (or separated) aldehyde is refluxed with an alkanol to form the acetal.

(5) The acetal is treated with a reducing agent, such as lithium aluminum hydride, in tetrahydrofuran, to give the cis 2-aminomethylcyclopropyl-1,1-dialkylacetal.

(6) The acetal is added to a cyanide in the presence of a liquid alkanecarboxylic acid to form the N-alkanoyl-3-azabicyclo(3.1.0)-hexane-2-carbonitrile.

(7) The nitrile is treated with a strong inorganic acid to give the N-alkanoyl-3-azabicyclo(3.1.0)hexane-2-carboxylic acid.

(8) The acid is treated with a strong inorganic acid to give 3-azabicyclo(3.1.0)hexane-2-carboxylic acid, as the salt of the inorganic acid.

Steps 7 and 8 can be combined, and effected without isolation of the N-alkanoyl intermediated.

(9) The free acid can be prepared from the salt by conventional procedures.

DESCRIPTION OF THE INVENTION

This invention is the above-described process for preparing 3-azabicyclo(3.1.0)hexane-2-carboxylic acid from a cis 2-aminomethylcyclopropyl-1,1-dialkyl acetal.

PREFERRED EMBODIMENTS

The invention is drawn to a process for the preparation of 3-azabicyclo(3.1.0)hexane-2-carboxylic acid (Compound I, hereinafter) of the formula

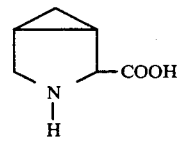

from a 2-aminomethylcyclopropyl-1,1-dialkylacetal (Formula II, hereinafter), of the formula:

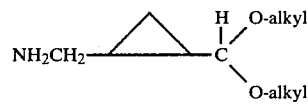

wherein each "alkyl" is the same and is alkyl of from one to four carbon atoms.

Conversion of a compound of Formula II to Compound I is effected by (a) effecting reaction between the compound of Formula II and a cyanide in the presence of an alkanecarboxylic acid of from 2 to 6 carbon atoms, RCOOH, to form the corresponding N-alkanoyl-3-azabicyclo(3.1.0)hexane-2-carbonitrile (Formula III, hereinafter), of the formula

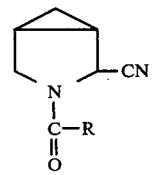

(b) treating the nitrile with a strong inorganic acid to form the corresponding N-alkanoyl-3-azabicyclo(3.1.0)hexane-2-carboxylic acid (Formula IV, hereinafter) of the formula

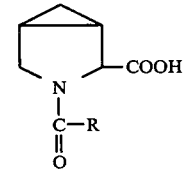

(c) treating the acid with a strong inorganic acid to form Compound I, as the salt of the inorganic acid.

In a preferred aspect of the process, the crude N-alkanoyl-3-bicyclo(3.1.0)hexane-2-carbonitrile (Formula III) is converted to the inorganic acid salt of Compound I in a single step, without isolation of the intermediate compound of Formula IV.

The starting materials—the cis 2-aminomethyl dialkyl acetals—and the intermediates—the N-alkanoyl-3-azabicyclo(3.0.1)hexane-2-carbonitriles, and the corresponding 2-carboxylic acids—are believed to be novel compounds, and form a part of the method of the invention.

The product of the method of the invention ordinarily is a mixture of the geometric and optical isomers of Compound I, since it contains at least one asymmetric carbon atom. If desired, the isomers may be isolated by known techniques and procedures.

In the acetal starting materials, the alkyl moieties suitably are either of straight-chain or branched-chain configuration and the aminomethyl moiety has a cis-relationship with respect to the acetal (—CH(O—alkyl)$_2$) moiety. Cis-2-amino-methylcyclopropane-1,1-methyl acetal is to be preferred. The acetals can be prepared as outlined hereinbefore, and as illustrated in Example 1, hereinafter.

The cyanide reagent can be characterized by the formula: M—CN, wherein M is hydrogen, an alkali metal or alkaline earth metal ion, the ammonium ion, or an alkyl-substituted ammonium ion, such as the tri- and tetramethylammonium ions. Also suitable are compounds which can generate hydrogen cyanide in situ, such as aldehyde and ketone cyanohydrins, particularly acetone cyanohydrin, methyl ethyl ketone cyanohydrin and acetaldehyde cyanohydrin. An alkali cyanide is a convenient source of the cyanide, preference being given to sodium or potassium cyanide. Good results are obtained as a rule when the cyanide is used in slight molar excess, e.g. up to 10%w based on the acetal.

The alkanecarboxylic acid suitably is any normally liquid straight-chain or branched-chain acid of up to six carbon atoms, such as, for example, acetic acid, propionic acid, butyric acid, and the like. Acetic acid is to be preferred.

Preferably an excess of the alkanecarboxylic acid is used, and the acid is used as solvent as well as reagent. Glacial acetic acid is of choice.

The reaction can normally be conducted at moderately elevated temperatures. Temperatures up to the boiling point of the alkanecarboxylic acid used can be used, preference being given to temperatures in the range of from 40° C. to 120° C.

A small amount of an alkyl or arylsulphonic acid, such as methanesulphonic acid or p-toluenesulphonic acid may also be present in the reaction mixture, as it has a catalytic effect on the reaction. The amount of the sulphonic acid applied normally lies in the range of 0.3–10%w, preferably 2–6%w of the acetal used.

The reaction is normally carried out at atmospheric pressure. If required, superatmospheric pressures—e.g., pressures up to 10 atmospheres—may be applied.

The reaction can also be carried out in the presence of a solvent, for instance, when the alkanecarboxylic acid is not used in a molar excess, or as a co-solvent. Ethers such as diethyl ether or tetrahydrofuran or aliphatic nitriles such as acetonitrile are suitable.

The product, 3-alkanoyl 3-azabicyclo(3.1.0)hexane-2-carbonitrile, can be isolated if necessary but normally this compound will be converted in situ into the corresponding carboxylic acid and thence to the salt of 3-azabicyclo(3.1.0)hexane-2-carboxylic acid by treating the reaction mixture containing the product with a strong acid such as hydrochloric acid. It will be appreciated that the free carboxylic acid can be liberated from the corresponding salt by using methods known in the art such as ion exchange techniques.

Esters of Compound I or acid addition salts thereof may be prepared by reaction of a compound of Formula III with an alcohol in the presence of an acid catalyst; for example, reaction with ethanol in the presence of dry hydrogen chloride leads to the ethyl ester. Preferred esters are those derived from alkanols having up to 6 carbon atoms.

The 3-azabicyclo(3.1.0)hexane-2-carboxylic acid prepared according to the process of this invention is usually obtained as a mixture of the appropriate cis/trans isomers, which each normally consists of the optical isomers involved. The cis/trans mixtures can be used as such, but they can also be separated into the individual isomers by methods known in the art—e.g., by using fractional crystallization techniques or ion exchange chromatographic techniques.

The invention is illustrated by the following Example. In all cases, the identities of the products involved were confirmed by appropriate chemical and spectral analyses.

EXAMPLE 1

Preparation of 3-azabicyclo(3.1.0)hexane-2-carboxylic Acid (a) Preparation of 2-cyanocyclopropyl-1,1-diethylacetal A mixture of 34.5 g of cis-ethyl 2-cyanocyclopropylcarboxylate in 120 ml of water was treated very slowly with a solution of 9.9 g of sodium hydroxide in 248 ml of water. The reaction mixture was washed with ether, acidified with concentrated HCl to give 2-cyanocyclopropyl carboxylic acid (1A).

27 ml of oxalyl chloride was added dropwise to a solution of 13.5 g of 1A in 60 ml of dry benzene at 70°–80° C. The reaction mixture was kept under reflux for two hours and then the solvent was evaporated under reduced pressure. The crude product obtained was dissolved in 100 ml of dry tetrahydrofuran and treated with a solution of tri-(tertbutoxy) lithium aluminium hydride at −60° C. in 150 ml of dry tetrahydrofuran. After stirring the reaction mixture for two hours at −60° C. it was poured onto ice and extracted with chloroform. Evaporation of chloroform from the extract gave 2-cyanocyclopropylaldehyde (1B).

A mixture of 8.1 g of 1B in 75 ml of ethanol was refluxed under stirring for two hours. The solution was then evaporated and 2-cyanocyclopropyl-1,1-diethylacetal, 1C, was obtained by distillation at 70°–71° C./8 Torr.

(b) Preparation of 2-aminomethylcyclopropyl-1,1-diethylacetal 9 g of 1C in 90 ml of dry tetrahydrofuran was added to lithium aluminium hydride in 250 ml of dry tetrahydrofuran at room temperature. After stirring the reaction mixture for 48 hours at ambient temperature 45 ml of a 10% solution of sodium hydroxide was added. The liquid was decanted and extracted with ether. Evaporation of the solvent gave 2-aminomethylcyclopropyl-1,1-diethylacetal, 1D.

(c) Preparation of 3-azabicyclo(3.1.0)hexane-2-carboxylic Acid 2 g of 1D was added to 6.8 g of potassium cyanide in 90 ml of glacial acetic acid and 0.2 ml of methanesulphonic acid at 40° C. The mixture was kept at 65° C. for 17 hours and then poured onto ice. After extraction, 3-acetyl 3-azabicyclo(3.1.0)hexane-2-carbonitrile was obtained. This product was dissolved in 6 N hydrochloric acid (about 100 ml) and refluxed during 6 hours. The hydrochloric acid salt of cis 3-azabicyclo(3.1.0)hexane-2-carboxylic acid was obtained. Pure cis-3-azabicyclo(3.1.0)hexane-2-carboxylic acid was obtained by treating the hydrochloric acid salt with copper (II) hydroxide and extracting the copper (II) salt formed with methanol followed by conversion of the salt into the final product by treatment with hydrogen sulfide to precipitate copper sulfide. The final product had n.m.r. characteristics consistent with published data.

We claim:

1. A compound of the formula:

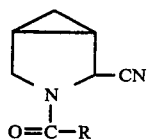

wherein R is alkyl of two to five carbon atoms.

2. A compound according to claim 1 wherein R is methyl.

3. A process for preparing a compound of claim 1 which comprises treating, at a temperature of from about 40° C. to about 120° C., an acetal of the formula

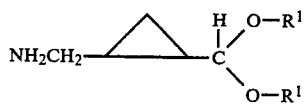

wherein each $R^1$ is alkyl of from one to four carbon atoms, said compound being in the cis-isomeric configuration, with up to ten percent stoichiometric excess of a cyanide in the presence of a stoichiometric excess of an alkanecarboxylic acid of two to five carbon atoms, optionally also in the presence of a solvent selected from one or both of (a) excess of the alkanecarboxylic acid, and (b) ethers and aliphatic nitriles, optionally also in the presence of from 0.3 to 10 percent by weight of the acetal of an alkyl or arylsulfonic acid, as catalyst.

4. A process for preparing a compound of claim 1 wherein cis-2-aminomethyldiethylacetal is treated, at a temperature of from about 40° C. to about 120° C., with up to about a ten percent stoichiometric excess of sodium or potassium cyanide in the presence of acetic acid as reagent and solvent, and in the presence of 0.3 to 10 percent, based on the acetal of methanesulfonic acid or p-toluenesulfonic acid, as catalyst.

* * * * *